(12) United States Patent
Miraki

(10) Patent No.: US 9,226,824 B2
(45) Date of Patent: Jan. 5, 2016

(54) SURGICAL STABILIZER AND CLOSURE SYSTEM

(75) Inventor: Manouchehr Miraki, Laguna Hills, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 1080 days.

(21) Appl. No.: 13/301,515

(22) Filed: Nov. 21, 2011

(65) Prior Publication Data

US 2012/0136200 A1 May 31, 2012

Related U.S. Application Data

(60) Provisional application No. 61/418,188, filed on Nov. 30, 2010.

(51) Int. Cl.
*A61F 2/24* (2006.01)
*A61B 17/34* (2006.01)
(Continued)

(52) U.S. Cl.
CPC ........... *A61F 2/2433* (2013.01); *A61B 17/3421* (2013.01); *A61B 17/3423* (2013.01); *A61M 25/04* (2013.01); *A61B 17/06166* (2013.01); *A61B 19/26* (2013.01);
(Continued)

(58) Field of Classification Search
CPC ........... A61B 2017/00243; A61B 2017/00247; A61B 17/0469; A61F 2/2418; A61F 2/2427
USPC ................. 623/2.11; 606/108, 222, 223, 226; 604/27, 28, 158, 264, 506
See application file for complete search history.

(56) References Cited

U.S. PATENT DOCUMENTS

| 4,573,470 A | 3/1986 | Samson et al. |
| 4,582,181 A | 4/1986 | Samson |

(Continued)

FOREIGN PATENT DOCUMENTS

| DE | 202010000329 U1 | 5/2010 |
| EP | 0815805 | 1/1998 |

(Continued)

OTHER PUBLICATIONS

Todd M. Dewey, et al., *Feasibility of a Trans-Apical Approach for Aortic Valve Implantation Using a Device Delivered Valve*, Abstract Presentation at ISMICS 8th Annual Meeting , Jun. 1-4, 2005 New York (pp. 1-2- of flier also attached).

(Continued)

*Primary Examiner* — Victor Nguyen
*Assistant Examiner* — Kevin Everage
(74) *Attorney, Agent, or Firm* — AnneMarie Kaiser; David L. Hauser

(57) ABSTRACT

A system for stabilizing the heart via a helical needle, providing access to the interior of the heart via an introducer sheath, and forming a purse string suture using suture delivered by the helical needle. A helical needle projects distally from the device and terminates in a sharp distal tip. The helical needle is advanced into the heart wall, and is used to stabilize the heart and to pass a purse string suture through the heart tissue. An access port provides access to the interior of the heart via an opening passing through the heart wall in an area circumscribed by the helical needle. The helical needle may have a deflection segment adjacent the distal tip that is more flexible than the rest of the helical distal portion of the helical needle.

10 Claims, 12 Drawing Sheets

(51) Int. Cl.
*A61M 25/04* (2006.01)
*A61B 17/06* (2006.01)
*A61B 19/00* (2006.01)
*A61B 17/00* (2006.01)
*A61B 17/04* (2006.01)
*A61M 25/00* (2006.01)

(52) U.S. Cl.
CPC .............. *A61B 2017/00247* (2013.01); *A61B 2017/00867* (2013.01); *A61B 2017/0406* (2013.01); *A61B 2017/061* (2013.01); *A61B 2017/06052* (2013.01); *A61B 2017/06076* (2013.01); *A61B 2017/3427* (2013.01); *A61F 2/2418* (2013.01); *A61M 2025/0095* (2013.01)

(56) References Cited

U.S. PATENT DOCUMENTS

| | | | |
|---|---|---|---|
| 4,944,740 | A | 7/1990 | Buchbinder et al. |
| 5,125,895 | A | 6/1992 | Buchbinder et al. |
| 5,571,215 | A | 11/1996 | Sterman et al. |
| 5,713,951 | A | 2/1998 | Garrison et al. |
| 5,820,631 | A | 10/1998 | Nobles |
| 5,968,068 | A | 10/1999 | Dehdashtian et al. |
| 6,033,378 | A | 3/2000 | Lundquist et al. |
| 6,071,273 | A | 6/2000 | Euteneuer et al. |
| 6,106,540 | A | 8/2000 | White et al. |
| 6,231,563 | B1 | 5/2001 | White et al. |
| 6,251,092 | B1 | 6/2001 | Qin et al. |
| 6,346,074 | B1 | 2/2002 | Roth |
| 6,379,372 | B1 | 4/2002 | Dehdashtian et al. |
| 6,540,782 | B1 | 4/2003 | Snyders |
| 6,626,917 | B1 | 9/2003 | Craig |
| 6,730,118 | B2 | 5/2004 | Spenser et al. |
| 6,821,297 | B2 | 11/2004 | Snyders |
| 6,893,460 | B2 | 5/2005 | Spenser et al. |
| 6,899,704 | B2 | 5/2005 | Sterman et al. |
| 6,908,481 | B2 | 6/2005 | Cribier |
| 7,780,723 | B2 | 8/2010 | Taylor |
| 7,803,185 | B2 | 9/2010 | Gabbay |
| 2001/0001812 | A1 | 5/2001 | Valley et al. |
| 2002/0128707 | A1 | 9/2002 | Kavteladze et al. |
| 2003/0109924 | A1 | 6/2003 | Cribier |
| 2004/0116897 | A1 | 6/2004 | Aboul-Hosn |
| 2005/0070844 | A1 | 3/2005 | Chow et al. |
| 2005/0148997 | A1 | 7/2005 | Valley et al. |
| 2005/0209671 | A1 | 9/2005 | Ton et al. |
| 2005/0240200 | A1 | 10/2005 | Bergheim |
| 2005/0251251 | A1 | 11/2005 | Cribier |
| 2005/0271844 | A1 | 12/2005 | Mapes et al. |
| 2006/0004439 | A1 | 1/2006 | Spenser et al. |
| 2006/0036265 | A1 | 2/2006 | Dant |
| 2006/0074484 | A1 | 4/2006 | Huber |
| 2006/0178675 | A1 | 8/2006 | Hamman |
| 2006/0271064 | A1 | 11/2006 | Agnew |
| 2009/0240264 | A1* | 9/2009 | Tuval .................. A61B 17/0469 606/148 |
| 2009/0287182 | A1 | 11/2009 | Bishop et al. |
| 2009/0287183 | A1 | 11/2009 | Bishop et al. |
| 2011/0028995 | A1* | 2/2011 | Miraki ............... A61B 17/0482 606/144 |

FOREIGN PATENT DOCUMENTS

| | | |
|---|---|---|
| EP | 1356793 | 10/2003 |
| EP | 1447111 | 8/2004 |
| WO | WO 2005/102015 | 11/2005 |
| WO | WO 2006/127765 | 11/2006 |
| WO | WO-2011017150 A2 | 2/2011 |

OTHER PUBLICATIONS

Liang MA, et al., *Double-crowned valved stents for off-pump mital valve repalcement*, European Journal of Cardio-Thoracic Surgery 28 (2005) pp. 194-199.

F. L. Wellens, *How Long Will the Heart Still Beat?*, Texas Heart Institute Journal, vol. 32, No. 2, 2005, pp. 126-129.

Christoph H. Huber, et al., *Direct-Access Valve Replacement a Novel Approach for Off-Pump Valve Implantation Using Valved Stents*, JACC, vol. 46, No. 2, 2005, pp. 366-370, www.content.onlinejacc.org by Susan Porter on Sep. 27, 2005.

Kevin A. Greer, et al., *Skeletal Muscle Ventricles, Left Ventricular Apex-to-Aorta Configuration*: 1-11 Weeks in Circulation, Circulation 95: 497-502.

Ferrari, M., et al., *Transarterial Aortic Valve Replacement With a Self-Expanding Stent in Pigs*. Heart 2004 90: 1326-1331.

* cited by examiner

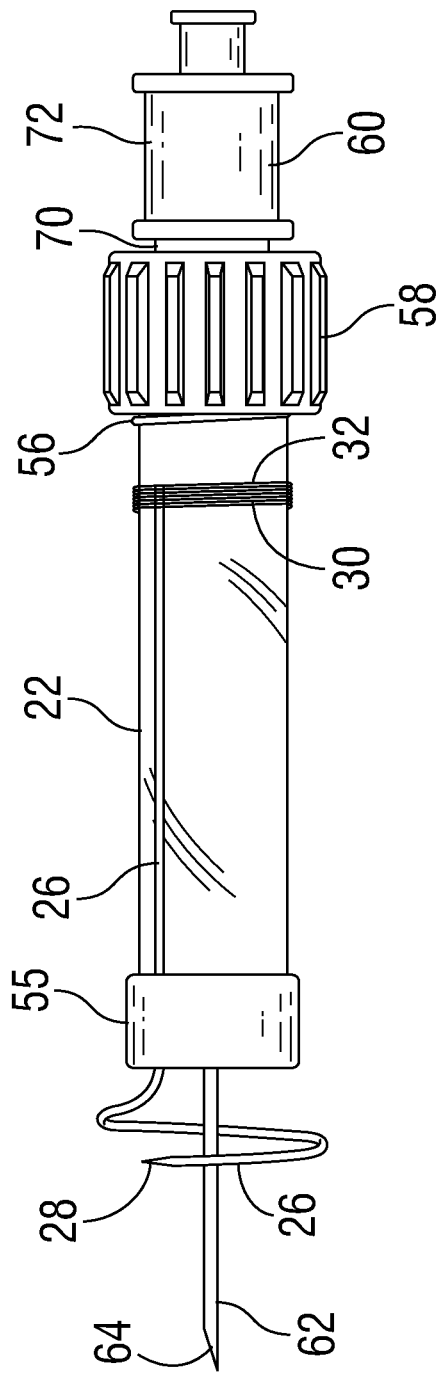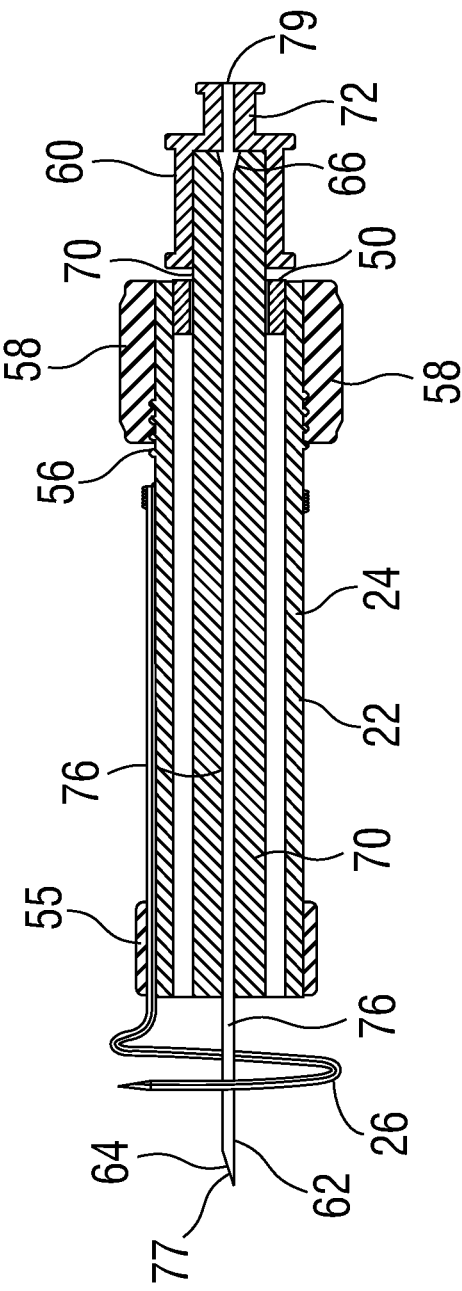

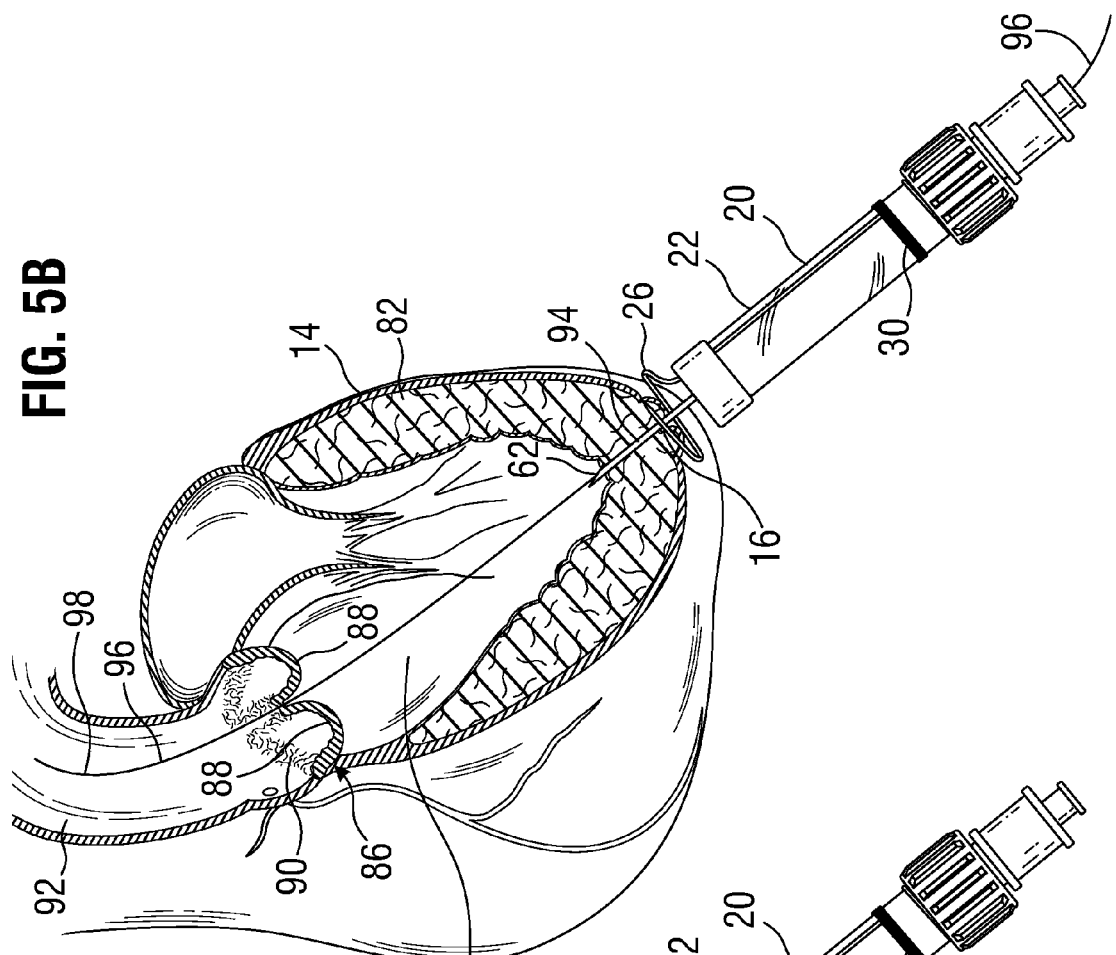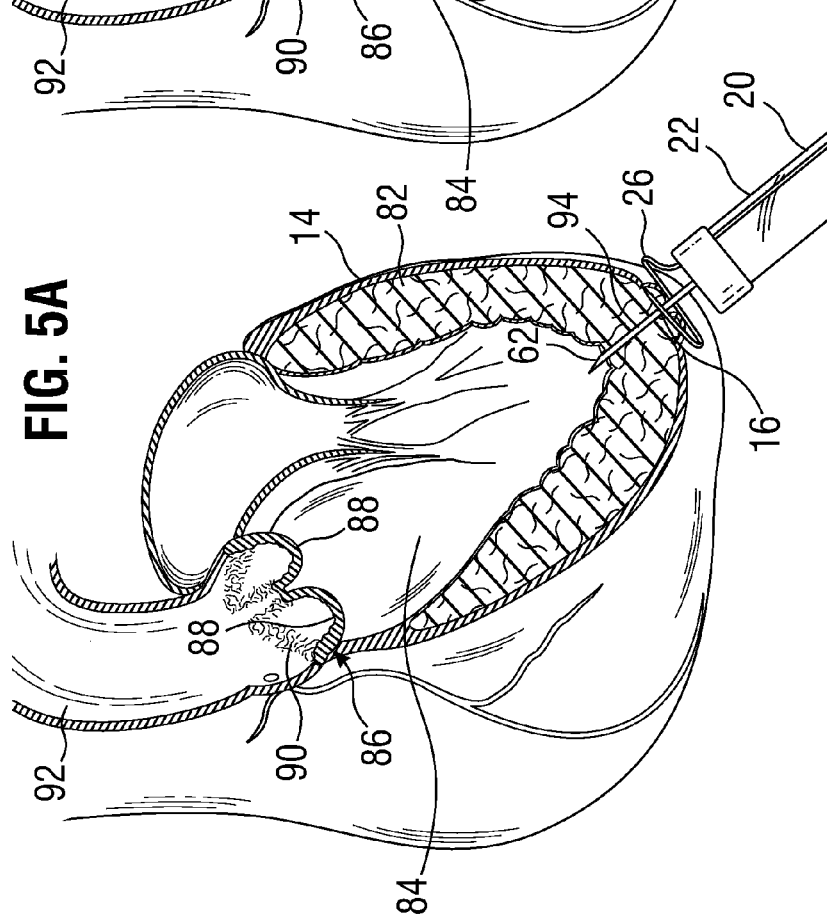

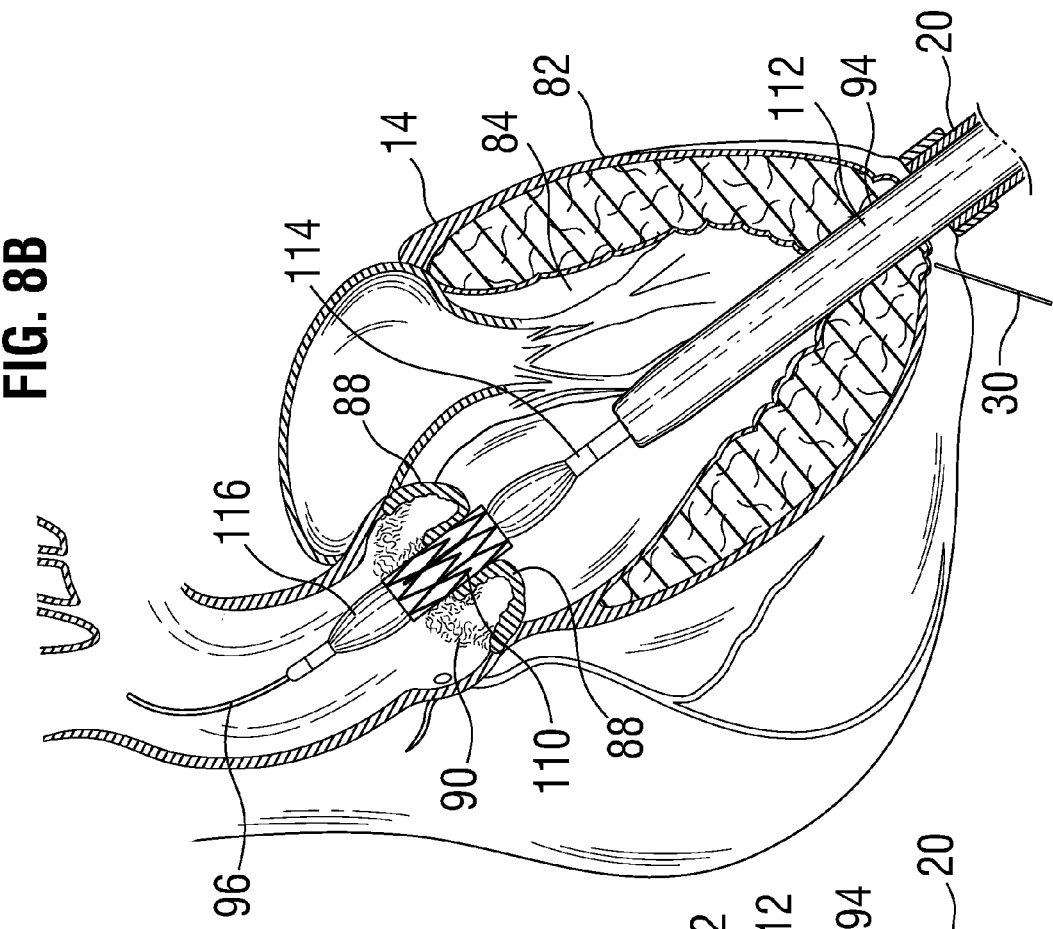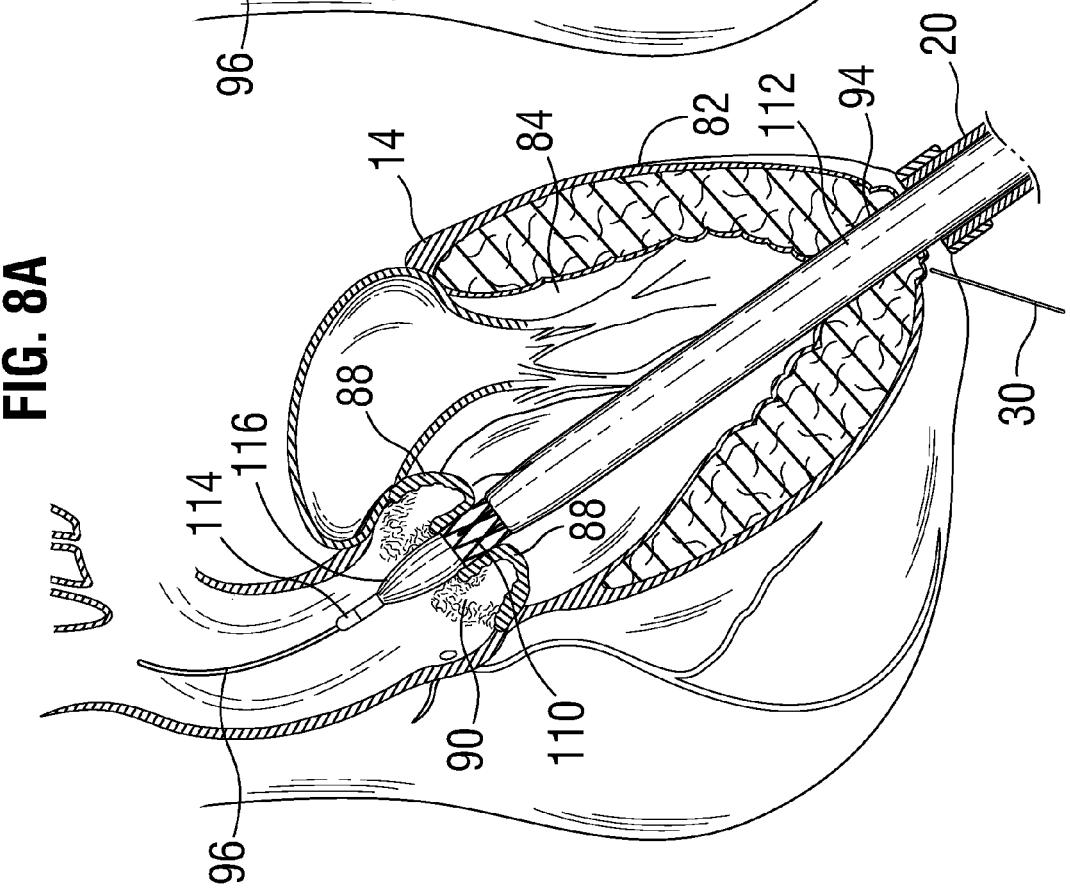

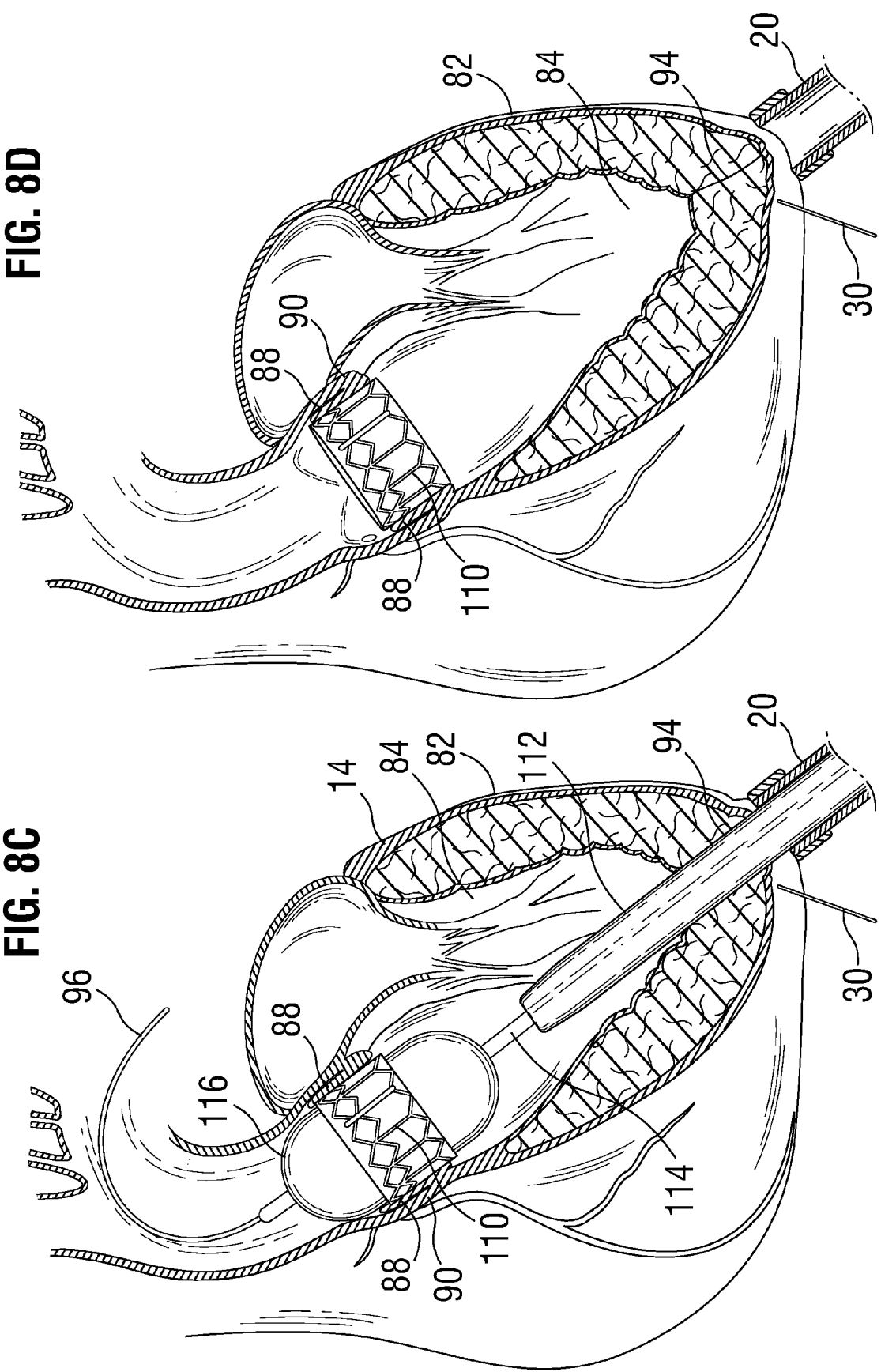

SURGICAL STABILIZER AND CLOSURE SYSTEM

RELATED APPLICATIONS

The present application claims priority under 35 U.S.C. §119 to U.S. Provisional Application Ser. No. 61/418,188, filed Nov. 30, 2010. This application is related to U.S. Provisional Patent Application No. 61/229,190 entitled "Surgical Puncture Cinch and Closure System," filed Jul. 28, 2009; to U.S. Provisional Patent Application No. 61/252,114 entitled "Surgical Puncture Cinch and Closure System," filed Oct. 15, 2009; and to U.S. Utility patent application Ser. No. 12/844,139, entitled "Surgical Puncture Cinch and Closure System," filed Jul. 27, 2010. The entire contents of each of these applications are expressly incorporated herein by reference.

FIELD OF THE INVENTION

The present invention relates to methods and systems for performing procedures on a heart, and more particularly to stabilizing the heart, accessing the heart interior via an opening in the heart wall, and closing the opening in the heart wall.

BACKGROUND OF THE INVENTION

The heart is a hollow muscular organ of a somewhat conical form; it lies between the lungs in the middle mediastinum and is enclosed in the pericardium. The heart generally rests obliquely in the chest behind the body of the sternum and adjoining parts of the rib cartilages, and typically projects farther into the left than into the right half of the thoracic cavity so that about one-third is situated on the right and two-thirds on the left of the median plane. The heart is subdivided by septa into right and left halves, and a constriction subdivides each half of the organ into two cavities, the upper cavity being called the atrium, the lower the ventricle. The heart therefore consists of four chambers; the right and left atria, and right and left ventricles, with one-way flow valves between respective atria and ventricles and at the outlet from the ventricles.

Heart valve repair and/or replacement may be indicated when there is a narrowing of a native heart valve, commonly referred to as stenosis, or when the native valve leaks or regurgitates, such as when the leaflets are calcified. Repairing a valve may include reshaping the valve annulus using, e.g., an annuloplasty ring, and/or repairing/replacing chordae tendinae, and/or repairing valve leaflets. When replacing the valve, the native valve may be excised and replaced with either a biologic or a mechanical valve.

Conventional heart valve surgery is an open-heart procedure conducted under general anesthesia, and is a highly invasive operation. The first 2-3 days following surgery are usually spent in an intensive care unit where heart functions can be closely monitored. The average hospital stay is between 1 to 2 weeks, with several more weeks to months required for complete recovery.

In recent years, advancements in minimally-invasive surgery and interventional cardiology have encouraged some investigators to pursue percutaneous repair and/or replacement of heart valves. Percutaneous Valve Technologies ("PVT"), formerly of Fort Lee, N.J. and now part of Edwards Lifesciences of Irvine, Calif., has developed a plastically- or balloon-expandable stent integrated with a bioprosthetic valve. The stent/valve device, now called the Edwards Sapien™ Heart Valve, is deployed across the native diseased valve to permanently hold the valve open, thereby alleviating a need to excise the native valve. The Edwards Sapien™ Heart Valve is designed for delivery with the RetroFlex™ delivery system in a cardiac catheterization laboratory under local anesthesia using fluoroscopic guidance, thereby avoiding general anesthesia and open-heart surgery.

Some researchers propose implanting prosthetic heart valves at the valve annulus using a direct-access transapical approach. See, e.g., U.S. Patent Publication No. 2006-0074484. For replacing an aortic valve, access can be gained via the left ventricular apex (LVA), which is directed downward, forward, and to the left in the patient's chest (from the perspective of the patient). The apex typically lies behind the fifth left intercostal space (or between the fourth and fifth), 8 to 9 cm from the mid-sternal line, and about 4 cm below and 2 mm to the medial side of the left mammary papilla. Access to the left ventricle may therefore be attained through an intercostal incision positioned over the fifth left intercostal space. Such an approach is often termed a "mini-thoracotomy," and lends itself to surgical operations on the heart carried out using one or more short tubes or "ports"—thus, the operations are often referred to as "port-access" procedures.

Dehdashtian in U.S. Patent Publication No. 2007-0112422 discloses a port-access delivery system for transapical delivery of a prosthetic heart valve including a balloon catheter having a steering mechanism thereon that passes through an access device such as an introducer. The surgeon forms a puncture in the apex with a needle, advances a guidewire, then a dilator, and finally the introducer. Purse string sutures are pre-installed around the puncture to seal against blood leakage around the various devices and provide a closure after the procedure. During the procedure the doctor/assistant is able to apply tension to the purse-string-suture, which prevents inadvertent blood loss. After the deployment of the heart valve, the purse sting-suture is then used to permanently close the opening of the heart by drawing concentric tension on the suture ends, and tying a secure knot. The aforementioned Edwards Sapien™ Heart Valve may be inserted transapically with the Ascendra™ delivery system, much like the system disclosed in Dehdashtian.

Often, direct- or port-access techniques are conducted or proposed for off-pump, aka "beating heart" procedures, in which the heart remains beating as opposed to the patient being placed on a cardiopulmonary bypass system. Challenges remain in stabilizing various instruments used during these procedures, as well as in stabilizing targeted patient tissues and/or organs. For example, a number of devices are available that directly contact the heart muscle for stabilizing an area around a cardiac artery for coronary artery bypass graft (CABG) procedures. These systems typically include a soft contact member having suction that brackets a coronary artery, or grabs and manipulates an area of the heart for better access. These systems are mostly concerned with holding still a discrete surface area of the heart for direct operation thereon, and are not designed for operations carried out by instruments that extend within the beating heart, i.e., for intracardiac procedures.

What has been needed is a system and method for stabilizing the heart and the operating instruments, providing access to the heart interior, and sealing tissue punctures at the conclusion of the procedure. The current invention meets these needs.

SUMMARY OF THE INVENTION

The present application provides a system and method for stabilizing the heart (e.g., at its apex) and instruments used thereon, for accessing the interior of the heart via a puncture or other opening in the heart wall, and for securely closing the puncture/opening in the heart wall at the conclusion of the procedure. The invention may include delivery of a prosthetic (i.e., replacement) heart valve to a native valve site via so-called keyhole surgery or other procedures conducted through the heart wall, with a purse string suture applied to the heart to seal the tissue around ports passed therethrough and/or to seal any punctures in the heart wall. More broadly, the methods and systems described herein may be utilized in the context of various cardiac and other surgeries that benefit from stabilizing of body organs, accessing organ interiors, and using a purse string to effectuate closure of a puncture wound or similar opening.

One exemplary aspect of the invention is a method of stabilizing the heart, which can be conducted during a beating-heart procedure. The method includes providing a stabilizer having a generally helical needle at its distal end. The generally helical needle is advanced into the tissue of the heart wall, e.g., at the heart apex. The generally helical needle holds the heart apex against the stabilizer, which stabilizes the heart apex while still permitting the heart to beat.

A further exemplary aspect of the invention is a method of accessing the heart interior. A needle or similar puncture device (or other device configured to create an opening in the heart wall) is advanced through the stabilizer and through/into the heart wall, where the needle creates a puncture through the heart wall.

A further exemplary aspect of the invention is a method of forming a closure at the site of puncture in the tissue. The method includes providing the stabilizer with a length of suture in the handle. The generally helical needle (used to secure the heart wall to the stabilizer) contains a free end of the length of suture. The helical needle has a distal portion projecting from the handle in a helical shape and terminating in a sharp distal tip. The system further comprises a puncture needle extending from a distal end of the stabilizer substantially along an axis of the helical distal portion of the helical needle, the puncture needle having a sharp tip to puncture tissue. The method involves passing the puncture needle through the stabilizer to extend distally therefrom, and forming a puncture through a heart wall with the puncture needle. A user advances the suture stabilizer in screw-like fashion to thereby advance and rotate the helical needle so that the sharp distal tip passes helically into tissue around the puncture needle and continues at least 270° therearound. A free end of a length of suture may directed out of the tissue and grasped. The user then removes the puncture needle from the stabilizer, leaving the stabilizer (with helical needle) secured to the heart wall. The user then advances one or more surgical or other tools/devices through the stabilizer and into the heart via the puncture created by the puncture needle, and performs a procedure on the heart interior using the one or more surgical and/or other devices. After the procedure within the heart interior is completed, the one or more surgical and/or other devices are removed from the patient. The user then reverses rotation of the helical needle so that it retracts from the tissue while the length of suture remains within the heart wall through the generally helical path through the heart tissue and around the puncture. The user can then grasp the opposing ends portions of the suture as they extend from the heart wall, and tighten the suture to form a purse-string closure about the puncture.

The handle of the stabilizer may have a chamber housing a suture spool, the length of suture being wound on the spool, whereby the method further includes allowing the length of suture to play off the spool when grasping the free end that emerges from the tissue and reversing rotation of the helical needle so that it retracts from the tissue. The helical needle may extend from a distal end of the stabilizer handle at points that are offset from a longitudinal axis of the handle. The longitudinal axis of the handle may be aligned with a helical axis of the helical portion of the helical suture needle. In one embodiment, the helical suture needle extends from the handle at a point offset from the longitudinal axis of the handle, while the puncture needle extends from a point generally aligned with the longitudinal axis of the handle.

The handle of the stabilizer may form and/or include an access port through which one or more instruments and/or other devices (implants, etc.) may be introduced into the heart interior (or the interior of another body organ to which the stabilizer is secured). The access port may include a seal configured to prevent the unwanted passage of fluid through the port while still permitting the introduction and removal of instruments and/or other devices therethrough. The seal may be configured to engage against instruments passed through the access port, and to thereby restrain the instruments and/or prevent leakage around the instruments through the access port.

In one embodiment, the helical needle includes a deflection segment adjacent the distal tip that is more flexible than the rest of the helical distal portion of the helical needle, and the method includes deflecting the deflection segment in a proximal direction to direct the free end of the length of suture back out of the tissue. Alternatively, the suture applicator may include an inner needle arranged to translate through the helical needle and extend from the distal tip thereof, and having a relaxed shape that conforms to the helical shape of the helical needle except at a distal end portion that has a proximal bend so that it deflects in a proximal direction when extended from the distal tip of the helical needle. The method therefore includes translating the inner needle along the helical needle so that the distal end portion extends from the distal tip thereof and deflects in a proximal direction to direct the free end of the length of suture out of the tissue. The inner needle may be hollow with the length of suture extending therethrough, with the method including deflecting the distal end portion of the inner needle out of the tissue and grasping the free end of the length of suture.

In accordance with a specific application of the aforementioned method, the site of puncture is the apex of a ventricle, such as the left ventricle, and the method further includes installing a guidewire through the puncture needle into the ventricle. The user passes a cardiac surgery device along the guidewire and into the ventricle and performs a cardiac surgery with the cardiac surgery device. The user then removes the cardiac surgery device from the heart and applies tension to the first and second free ends of the length of suture to cinch the heart wall tissue and close the puncture.

In one application, the site of puncture is the apex of the left ventricle, and the cardiac surgery device includes an introducer sheath carrying a heart valve. In that case, the method may also include performing a heart valve replacement using the introducer sheath extending through the stabilizer device and the puncture, removing the introducer sheath from the stabilizer device and the puncture, removing the stabilizer, and tying the first and second free ends of the length of suture to form a purse string closure at the puncture.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

Features and advantages of the present invention will become appreciated as the same become better understood with reference to the specification, claims, and appended drawings wherein:

FIGS. 4A-4B are side and side (cross-sectional views) of a stabilizer device assembled with a puncture device according to an embodiment of the invention;

FIGS. 5A-5C are side cross-sectional views of a patient's heart depicting securing the stabilizer device to the heart apex according to an embodiment of the invention;

FIGS. 8A-8D are cross-sectional views through the left side of a patient's heart showing deployment of a prosthetic heart valve via a stabilizer device according to an embodiment of the invention;

DETAILED DESCRIPTION OF THE PREFERRED EMBODIMENTS

Figure 1:
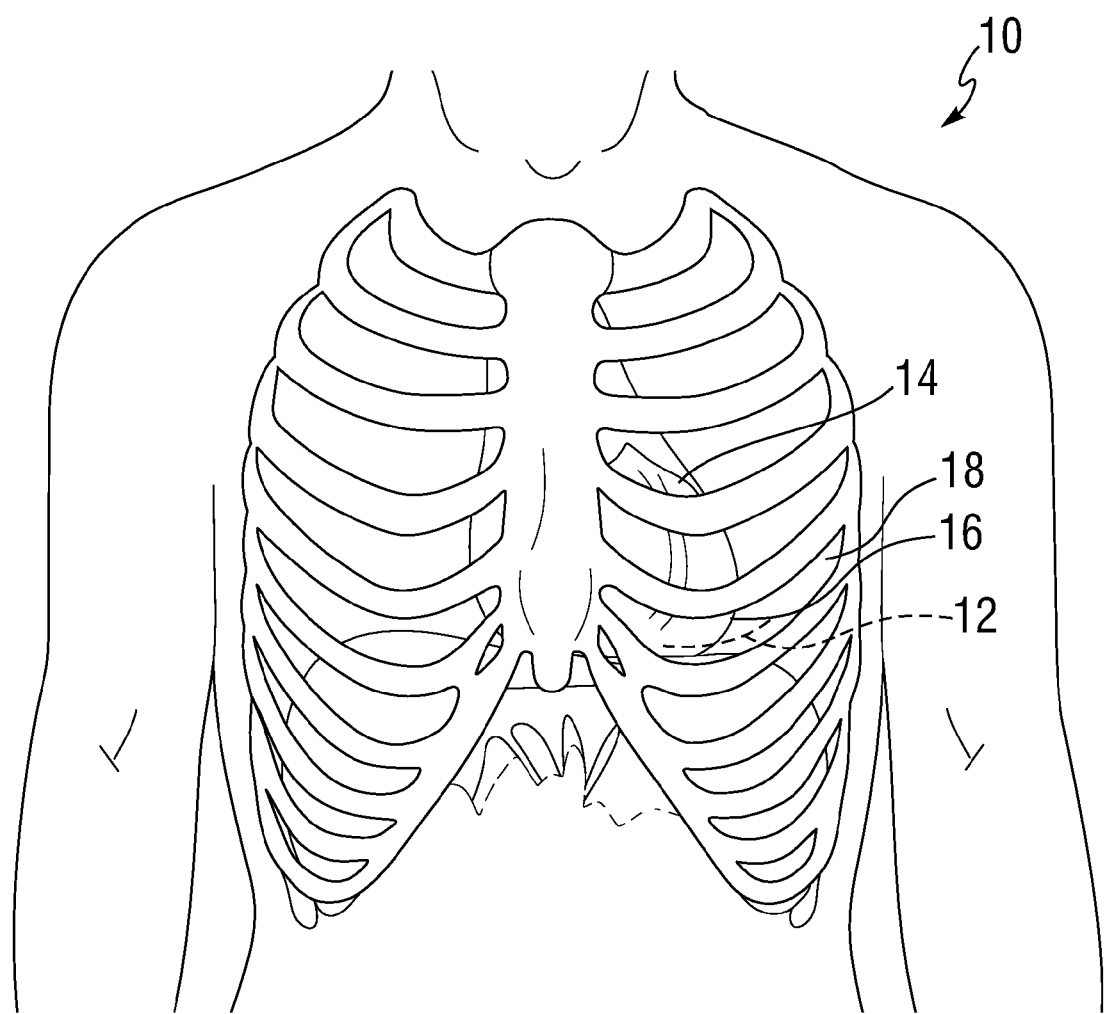
FIG. 1 is a schematic frontal view of a patient showing the location of an intercostal incision providing access to the apex of the left ventricle of the heart.
Figure 2A:
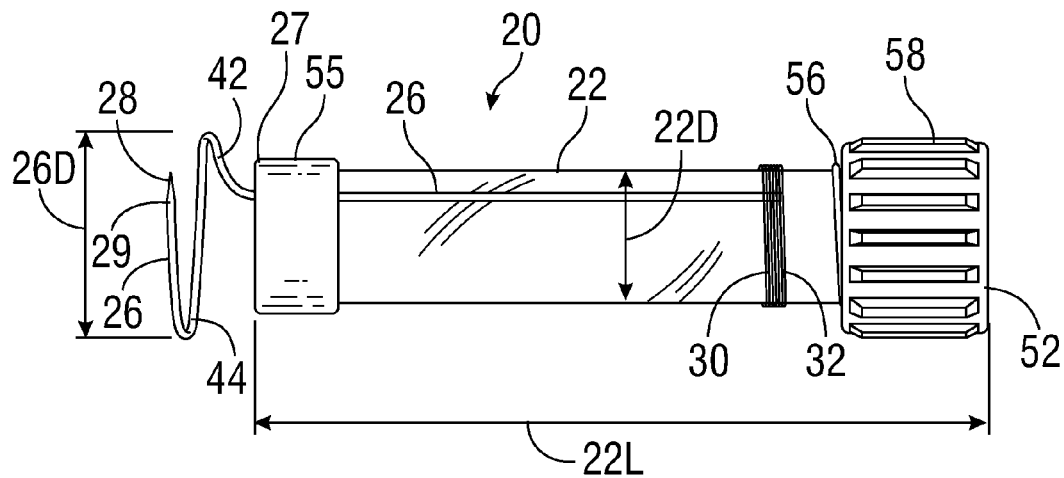
FIGS. 2A-2D are side, side (cross-sectional), front, and close-up views of a stabilizer device according to an embodiment of the invention.
Figure 2B:
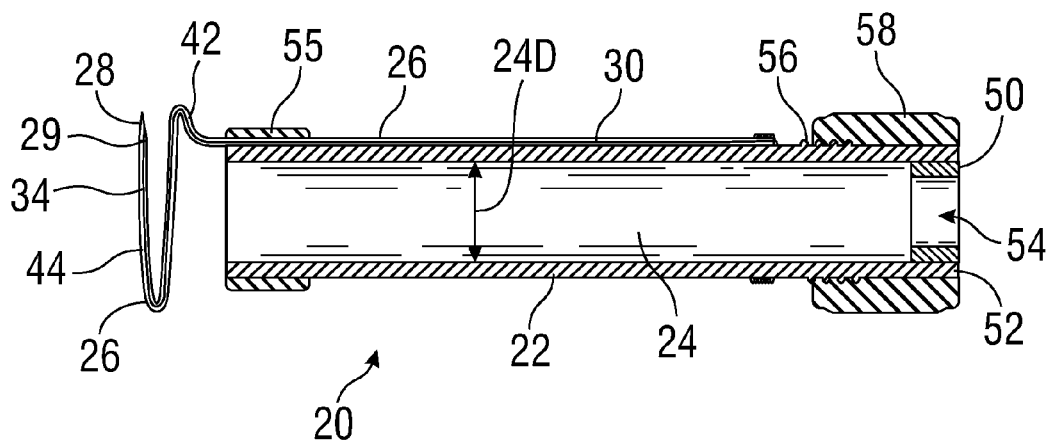
Figure 2C:
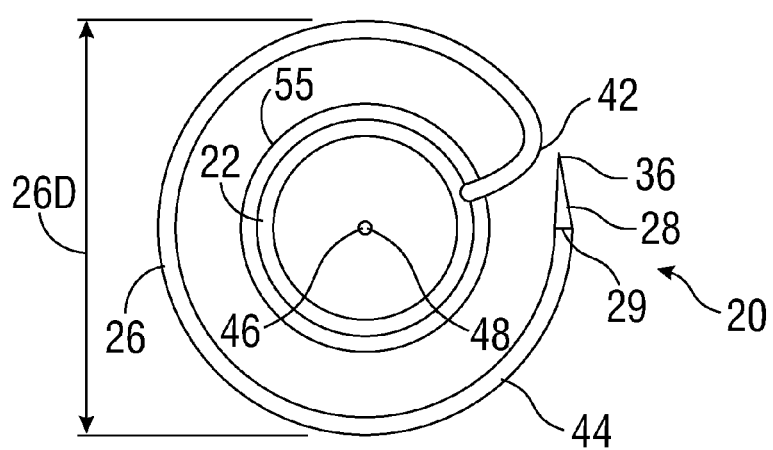
Figure 2D:
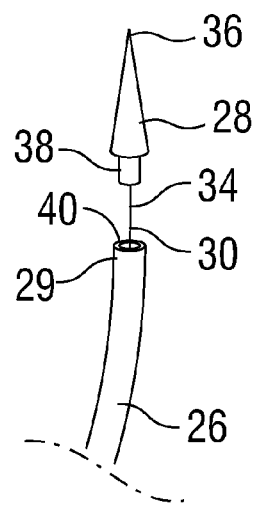

FIG. 1 depicts a cross-sectional view of a patient 10 where an intercostal incision opening 12 is created to access the patient's heart 14. The heart is a hollow muscular organ of a somewhat conical form, positioned between the lungs in the middle mediastinum and enclosed within the pericardium. The heart rests obliquely in the chest behind the body of the sternum and adjoining parts of the rib cartilages, and generally projects farther into the left than into the right half of the thoracic cavity so that about one-third is situated on the right and two-thirds on the left of the median plane. The heart is subdivided by septa into right and left halves, and a constriction subdivides each half of the organ into two cavities, the upper cavity being called the atrium, the lower the ventricle. The heart therefore consists of four chambers; the right and left atria, and right and left ventricles.

As seen in FIG. 1, the left ventricular apex (aka LVA) 16 is directed downward, forward, and to the left (from the perspective of the patient). The left ventricular apex 16 typically lies behind the fifth left intercostal space 18 (i.e., between the fifth and sixth ribs), generally 8 to 9 cm from the mid-sternal line, and about 4 cm below and 2 mm to the medial side of the left mammary papilla. Access to the left ventricle may therefore be attained through the intercostal incision 12 as shown in dashed line, positioned adjacent the fifth left intercostal space 18. Such an approach is often termed a "mini-thoracotomy," and lends itself to surgical operations on the heart carried out using one or more short tubes or "ports"—thus, the operations are often referred to as "port-access" procedures.

FIGS. 2A-2D depict a stabilizer device 20 according to an embodiment of the invention. The device 20 includes a main body 22, which may act as a handle as well as an access port. The main body 22 may be a generally elongated and tubular member having a length 22L and outer diameter 22D. In one embodiment, the length 22L is about 2-4 inches, and the outer diameter 22D is about 0.35-0.60 inches, although these dimensions are exemplary. The main body 22 may include an inner lumen 24 having a diameter 24D, which in one exemplary embodiment may be about 0.25-0.50 inches.

The device 20 includes a generally helical needle 26 extending from the distal end 27 of the main body 22. The helical needle 26 may be secured to the main body 22 via bonding or other techniques, and may be formed from a hypotube, e.g., a 18 gauge hypotube, formed to define a generally helical shape having a diameter 26D, wherein in one embodiment the diameter is in the range of about 20 mm-25 mm. In the particular embodiment depicted, a sharp detachable needle tip 28 is positioned at the distal portion 29 of the helical needle 26. A line of suture 30 passes from the main body 22 through the helical needle 26. A proximal portion 32 of the suture 30 is secured to the main body 22 (such as by being wrapped therearound or placed inside a cavity within the main body), and a distal portion 34 of the suture 30 is secured to the detachable needle tip 28. The detachable needle tip 28 includes a sharp distal point 36 and a crimped proximal portion 38, with the crimped proximal portion 38 sized and shaped to fit relatively tightly into the distal opening 40 of the helical needle 26 to form a smooth transition from the helical needle 26 to the detachable needle tip 28. This will allow for smooth penetration of the helical needle 26 through the desired tissue. In the embodiment depicted in FIGS. 2A-2C, the helical needle 26 includes a transition section 42 extending from the distal end 27 of the main body 22. The transition section 42 leads to the main helical section 44. The main helical section 44, when viewed in an end view such as in FIG. 2C, forms a generally 360 degree circular form, with the central axis 46 of the helical 360-degree pattern of the main helical section 44 aligned with the central axis 48 of the main body 22. Note that the 360 degree helical needle is only one embodiment of the invention. For example, the helical needle may define a path that encompasses more than 360 degrees, or less than 360 degrees, depending on the particular application. In one embodiment, the helical needle passes through a partial circular path defining only 270 degrees or even less.

The main body 22 may include a seal to prevent and/or otherwise control the passage of fluids and or other material(s) through the inner lumen 24. In the example of FIGS. 2A-2D, the main body 22 includes a silicon washer 50 fitted within the main body proximal end 52. The silicon washer 50 has an internal opening 54. The main body proximal end 52 includes a threaded fitting 56 which can accommodate a cap 58 having a matching thread. The cap 58 is screwed onto the threaded fitting 56. As the cap 58 is advanced (i.e., tightened), it produces inward pressure on the main body 22 and thus on the outside of the silicon washer 50. The silicon washer 50 is thus compressed, reducing the diameter of the internal opening 54 so that the silicon washer 50 will compress against anything advanced through the internal opening 54.

The main body 22 may also include a distal ring 55, which may be formed from a relatively soft material. The distal ring 55 in the embodiment depicted helps to secure the helical needle 26 to the main body 22 and may also act as a padding element to protect the heart tissue. The distal ring 55 may extend distally from the rest of the main body 22, so that it would define the distal-most portion of the device other than the helical screw, and thus provide extra padding when the device is placed against the heart wall.

Figure 3A:
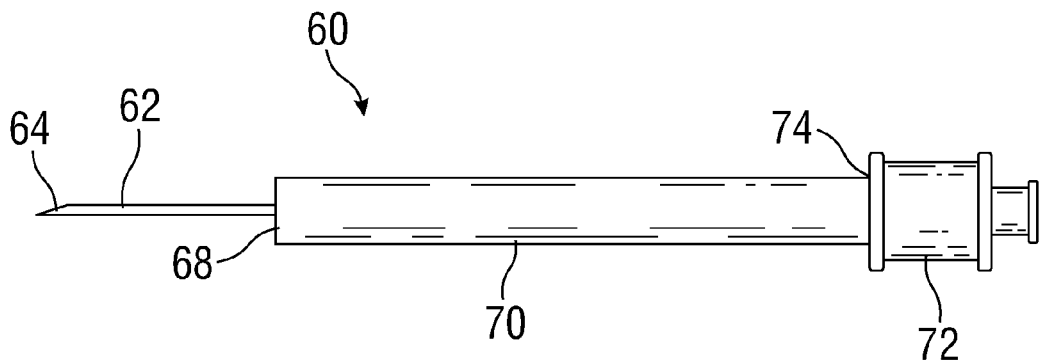
FIG. 3A-3C side, side (cross-sectional), and front views of a puncture device according to an embodiment of the invention.
Figure 3B:
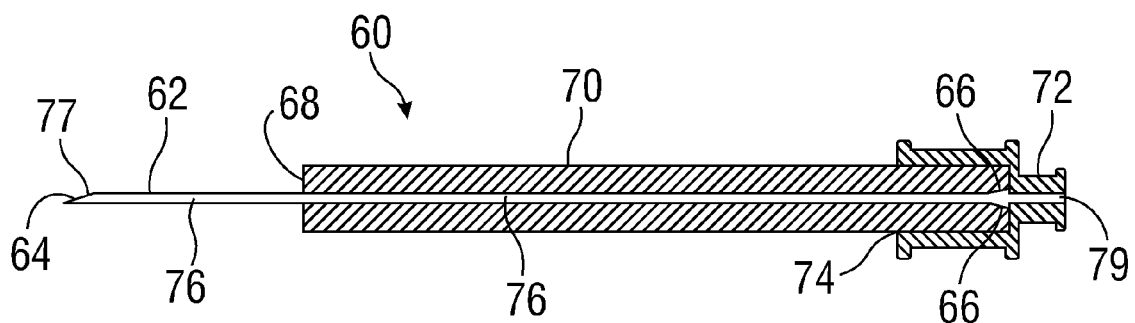
Figure 3C:
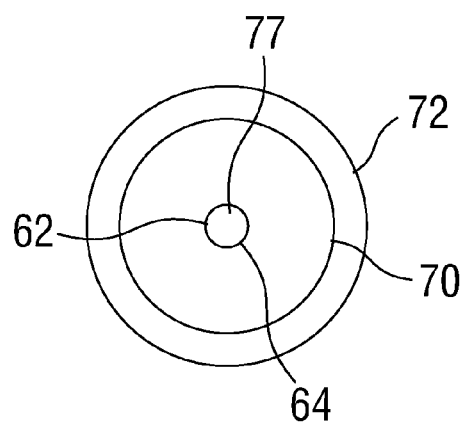

As depicted in FIGS. 3A-3C, a further element is a puncture needle assembly 60, which includes a puncture needle 62. The puncture needle 62 may have a sharp distal tip 64 and/or a flared proximal end 66. In an embodiment of the invention, the puncture needle is an 18-gauge hypotube having a length of about 3-4.5 inches, which is sufficient to pass through the wall of a human heart. A female luer 72 is secured to the proximal end 74 of the single lumen tube 70. In the particular embodiment depicted, the needle 62 is bonded to or otherwise lies within the entire length of body 70, with the flared proximal end 66 residing at the luer 72.

The puncture needle 62 includes an inner lumen 76 and distal opening 77. The luer lock includes a proximal opening 79. The puncture needle lumen 76, puncture needle distal opening 77, and luer lock proximal opening 79 each has sufficient diameter to accommodate a guide wire, such as a 0.035 inch guide wire. The puncture needle assembly 60 is thus sized and configured to permit a guide wire (not shown in FIGS. 3A-3C) to be introduced through the luer lock proximal opening 79, advanced through the puncture needle inner lumen 76, and out the puncture needle distal opening 77.

As depicted in FIGS. 4A-4B, the puncture needle assembly 60 can be advanced through the inner lumen 24 of the device 20 until the puncture needle distal tip 64 extends distally from the device main body 22 and distally past the helical needle 26. Note that the puncture needle assembly 60 can even be advanced further than shown, depending on the particular application, such that the puncture needle body 70 also extends distally at least partially from the device main body 22. Luer 72 may have too large an outer diameter to pass through the main body lumen 24, and will instead engage against the cap 58 and/or main body proximal end 52 to prevent the puncture needle assembly 60 from being advanced too far through the device 20. The lumen tube 70 fits tightly within the opening in the washer 50, so that when the cap 58 is tightened the washer 50 engages inwardly against the lumen tube 70 to hold the puncture needle assembly 60 and/or to form a tight seal between the puncture needle assembly/lumen tube 70 and the device main body 22. Such a tight seal may prevent and/or otherwise control the passage of fluids therethrough.

FIG. 5A illustrates a stabilizer device 20 according to an embodiment of the invention placed adjacent the heart 14 at the left ventricular apex 16 thereof. The heart 14 includes a heart wall 82, left ventricle 84, aortic valve 86, aortic valve leaflets 88, aortic valve annulus 90, and aorta 92. The puncture needle 62 is advanced distally from the body 22 of the stabilizer device 20, creating a puncture 94 in the heart wall 82 at the apex 16. The puncture needle 62 is passed through the heart wall 82 and into the left ventricle 84. The puncture needle 62 has a length sufficient to pass through the heart wall 82 adjacent the apex 16. The main body 22 of the stabilizer device 20 may have sufficient length to reach from the heart apex to the position adjacent to and/or just outside of the intercostal access incision or other access point into the patient.

FIG. 5B illustrates a guidewire 96 being advanced through the stabilizer device 20 and puncture needle 62. The guidewire 96 is advanced through the left ventricle 84 and through the aortic valve annulus 90 until the guidewire distal end 98 is positioned in the aorta 92. In a preferred embodiment, the guide wire 96 has sufficient length to reach from the outside of the patient (adjacent the intercostal access incision or other access point) and into the aorta 92 via the heart apex 16. In one embodiment of the invention, the guidewire is a 0.035" diameter guidewire.

Figure 5C:
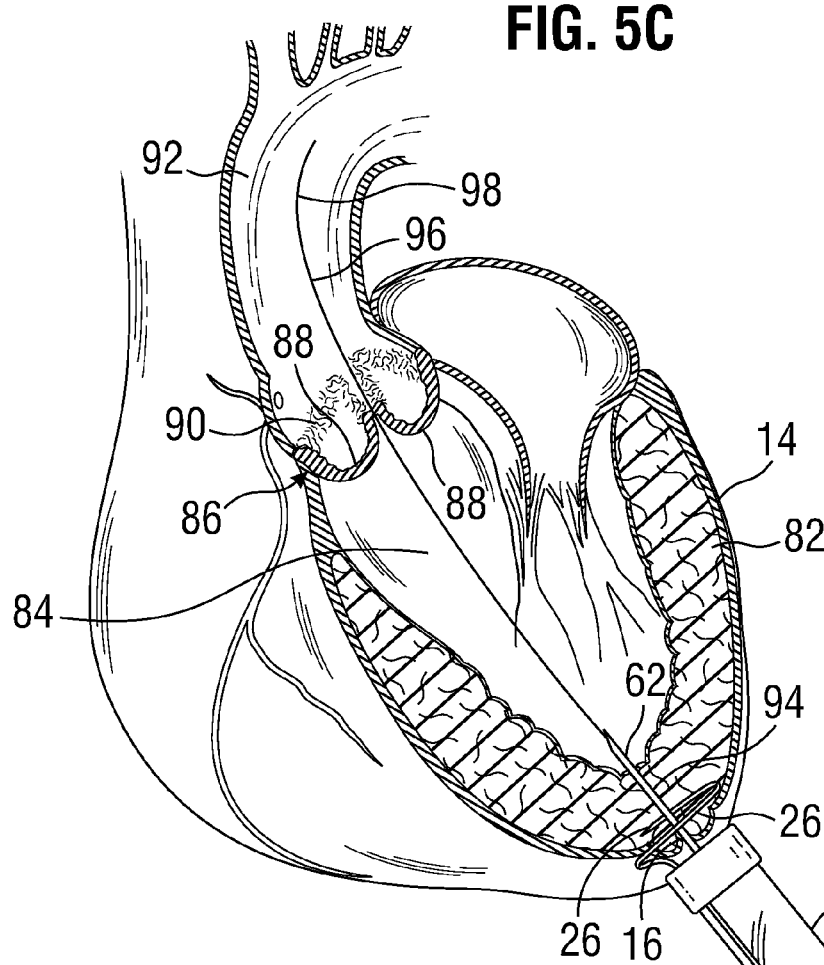

FIG. 5C depicts the helical needle 26 of the stabilizer device 20 being advanced into the heart wall 82 adjacent the apex 16. The surgeon or other user can grasp and apply forward force to the main body 22 of the stabilizer device 20 in order to press the distal tip 36 of the helical needle assembly against the apex 16, and simultaneously rotate the main body 22 of the stabilizer device 20 in order to rotate the helical needle 26 with respect to the heart 14. The rotation may be a partial rotation of about 270 degrees, although a full rotation of about 360 degrees (or more) may be preferable, depending on the particular application and/or characteristics of the specific stabilizer being used. The forward pressure and rotation of the helical needle 26 advances the helical needle 26, in screw-like fashion, into the heart wall 82. As the helical needle 26 advances into the heart wall 82, it follows a helical path around the puncture needle 62 and puncture 94 (i.e., with the puncture needle 62 and puncture 94 generally aligned with the central axis of the helical needle 26).

Figure 6:
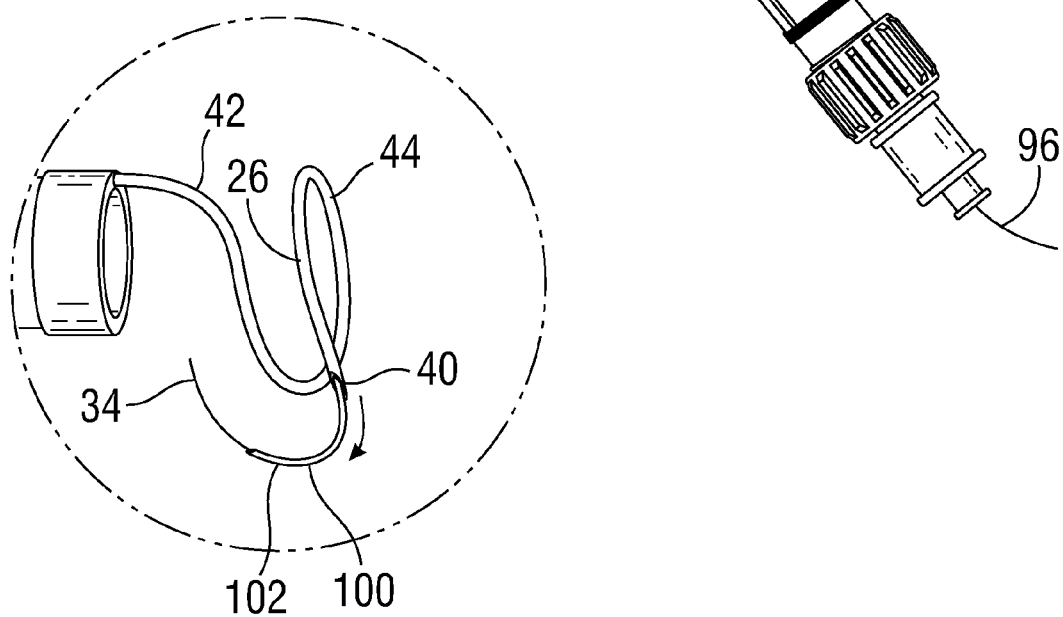
FIG. 6 is a close-up view of the distal portion of a stabilizer device according to an embodiment of the invention.

While the embodiments described above envision the helical needle 26 to have a detachable sharp tip, the invention is not limited to such embodiments. For example, a sharpened distal tip may be formed as an integral part of the helical needle (e.g., by sharpening the distal end of the hypotube) or as separate element, e.g., an inner needle with a sharp tip that can extend from within the helical needle (as depicted in FIG. 6), and/or a detachable sharp tip positioned at the distal end of the hypotube that forms of the helical needed (as depicted in FIGS. 2A-2D).

In one embodiment of the invention, after or as the helical needle is rotated into the heart wall 82, the distal end of the helical needle 26 is advanced back out of the heart wall 82 so that the surgeon or other user can grasp the distal portion 34 of the suture 30 in order to form the full purse-string. For example, when the helical needle 26 has been rotated about 360 degrees in screw-like fashion in the heart wall 82, the distal end of the helical needle 26 (such as the detachable distal tip 28 of FIGS. 2A-2D) can be advanced back out of the heart wall 82 at a position at or adjacent the position where the helical needle 26 first entered the heart wall 82, such as in the embodiment depicted in FIG. 7.

Advancing the distal end of the helical needle 26 out of the heart wall 82 may be achieved by various methods, depending on the particular application. For example, simply angling the entire instrument 20 can cause the distal end of the helical needle 26 to be directed in a generally proximal direction and back out of the heart wall 82. However, in other embodiments (which may be useful in circumstances such as where the tissue is somewhat fragile), a wire guide or deflection mechanism may be provided to assist the redirection of the helical needle distal end and/or suture distal portion. For example, in another embodiment of the invention, as depicted in FIG. 6, the helical needle 26 includes an inner needle 100 coaxially placed inside the helical needle 26. The inner needle 100 may be formed of a shape memory material, e.g., it may be made from a high elasticity material such as Nitinol. The inner needle 100 may be formed with a "programmed" shape generally the same as the helical needle 26, so as to slide more easily therein, but a distal portion 102 (e.g., about the last 1 inch) of the inner needle 100 may have a "memory" curve of about 90 degrees. Accordingly, when the inner needle distal portion 102 is advanced out of the distal end of the helical needle 26, the inner needle distal portion 102 (with the suture distal portion 34 extending from and/or secured to the inner needle distal portion 102) will turn back toward the main body 22 of the device 20, and thus advance back out of the heart wall 82 toward the device main body 22. Such an assembly is similar to that depicted in FIGS. 18A-B and 19A-19B of co-pending U.S. patent application Ser. No. 12/844,139, entitled "Surgical Puncture Cinch and Closure System," filed Jul. 27, 2010, the entire contents of each of which are expressly incorporated herein by reference.

With the suture distal portion 34 extending from, and/or otherwise advanced out of, the helical needle distal end and out of the heart wall, the surgeon or other user can then grasp the suture distal portion 34, such as by using a pair of forceps. Once the surgeon or other user has grasped the distal portion 34 of the suture 30, that distal portion 34 can be pulled away from the heart apex 16 and secured to a desired location. For example, the distal portion 34 could be pulled back out of the patient and temporarily secured to a desired location, such as an exterior surface of the patient (e.g., the patient's skin) at a location adjacent the incision. The suture 30 will thus pass from the device main body 22, through the helical needle 26 to follow a generally circular path through the heart wall and around the puncture 94 in the apex 16, and out of the patient.

Figure 7:
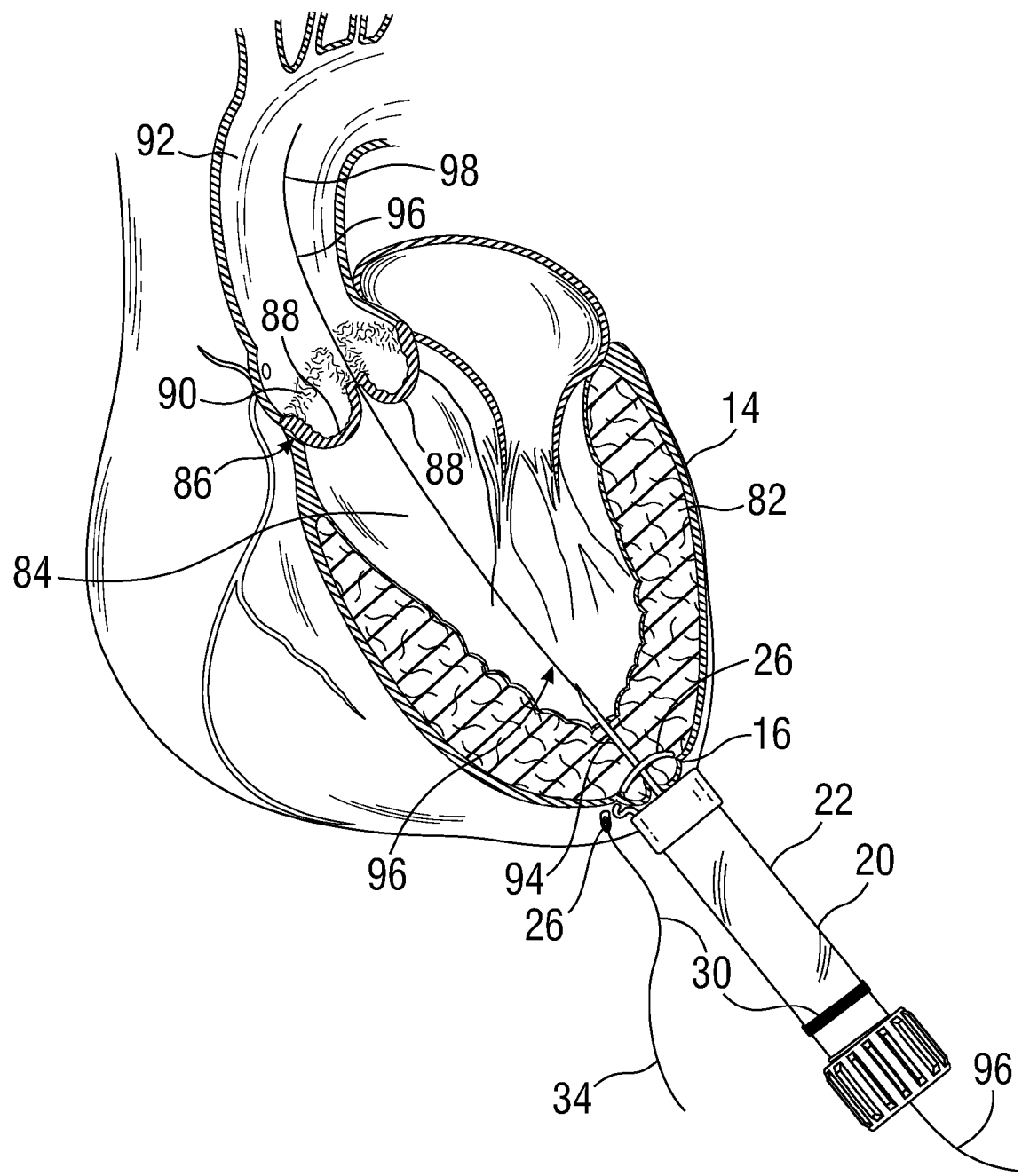
FIG. 7 is a side cross-sectional view of a patient's heart depicting the stabilizer device secured to the heart apex according to an embodiment of the invention

With the stabilizer device 20 secured firmly to the heart apex 16 via the helical needle 26, and with the distal portion 34 of the suture 30 secured to the outside of the patient, the puncture needle 62 is withdrawn from the heart 14 and from the stabilizer device main body 22, as depicted in FIG. 7. The stabilizer device 20 remains secured to the heart wall 82 and the guide wire 96 remains in place within the heart 14.

With the stabilizer 20 secured to the heart 14, the desired procedure may be performed within the interior of the heart 14. In one example of such a procedure, depicted in FIGS. 8A-8D, a prosthetic heart valve 110 is deployed in the heart 14. As seen in FIG. 8A, a sheath 112 is advanced into the heart 14 through the stabilizer device 20 and apical puncture 94 to a desired location within the ventricle 84. A deployment catheter 114 extends from the sheath. The distal portion of the deployment catheter 114 has an expandable balloon 116, and an expandable prosthetic heart valve 110 is positioned on the expandable balloon. As depicted in FIG. 8B, the deployment catheter 114 is advanced and maneuvered such that the expandable balloon 116 and expandable prosthetic heart valve 110 are at a desired position, which in FIG. 8B is a position between the valve leaflets 88 and within the valve annulus 90. With the deployment catheter 114 and prosthetic heart valve 110 at the desired position, the prosthetic heart valve 110 is expanded into contact with the tissue of the valve annulus and leaflets 88, with the existing valve leaflets 88 pressed between the expandable prosthetic heart valve 110 and the valve annulus 90. Expansion of the prosthetic heart valve 110 is accomplished by expanding the expandable balloon 116, as depicted in FIG. 8C. After the prosthetic heart valve 110 is deployed, the balloon 116 is deflated, and the deployment catheter 114 and sheath 112 are withdrawn from the patient.

Note that other medical devices and procedures may also be used with the stabilizer. For example, the prosthetic heart valve could be a self-expanding heart valve (such as a prosthetic heart valve having a support stent made of a memory material such as Nitinol), and the catheter may include a retractable sleeve that initially restrains the self-expanding heart valve but is then withdrawn to release the self-expanding heart valve, whereupon the self-expanding heart valve expands into the desired position, e.g., into contact with the valve annulus and/or leaflets. As another example, the catheter may be a suturing catheter configured to deliver a first end of suture through a native valve leaflet and deliver a second end of the suture through papillary muscles in order to create artificial chordae.

Details of an exemplary procedure for implanting a prosthetic heart valve (and which could be used in conjunction with the stabilizer devices and methods disclosed herein) are included in U.S. patent application Ser. No. 12/835,546, filed Jul. 13, 2010 and entitled "Transapical Delivery System for Heart Valves," and in U.S. patent application Ser. No. 12/835,555, filed Jul. 13, 2010 and entitled "Transapical Delivery System for Heart Valves," the contents of each of which are expressly incorporated herein in their entirety.

Figure 9A:
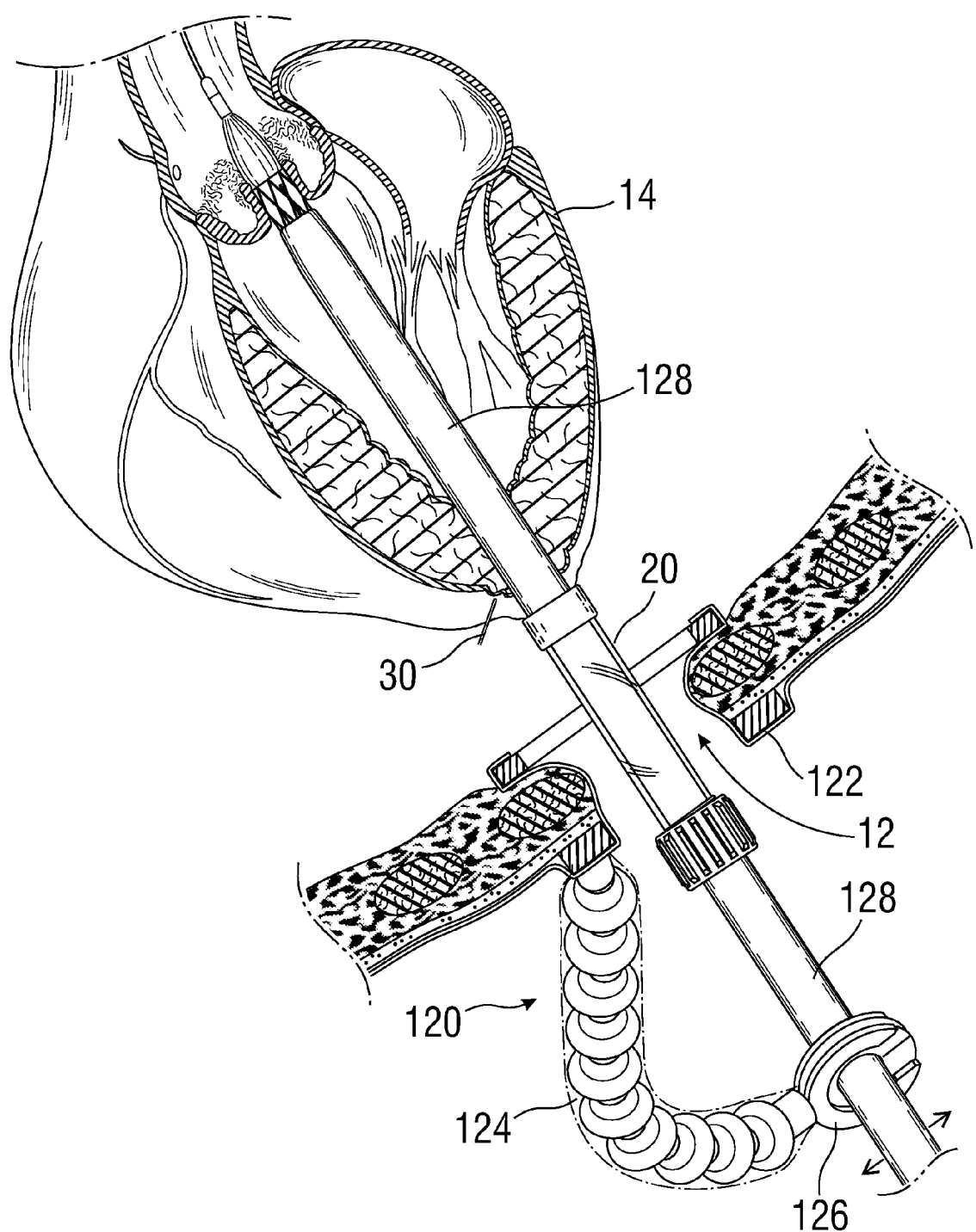
FIGS. 9A-9B are cross-sectional views of a patient's chest cavity depicting a stabilizer device and sheath being secured via a stabilizer platform positioned on the outside of the patient according to an embodiment of the invention.

The devices and methods disclosed herein could also be used with various other medical instruments and devices. For example, the device depicted in FIGS. 2A-4B could be used with a device stabilizer, such as that disclosed in U.S. Provisional Patent Application No. 61/229,675 filed Jul. 29, 2009 and entitled "Intracardiac Sheath Stabilizer," and in U.S. patent application Ser. No. 12/845,584, filed Jul. 28, 2010 and entitled "Intracardiac Sheath Stabilizer," the contents of each of which are expressly incorporated hereby in their entirety. For example, in FIG. 9A, a port-access stabilizer 120 has a base 122 secured to the patient adjacent the intercostal incision 12 (or other opening into a patient). The port-access stabilizer 120 has an articulated arm 124 with a cuff 126 which holds a sheath 128, with the sheath 128 advanced through the stabilizer device 20 and into the heart 14. The stabilizer arm 124 thus stabilizes the sheath 128, thereby also providing some stability for the stabilizer device 20. If the sheath 128 or other instrument were relatively restrained longitudinally with respect to the stabilizer device 20 (e.g., where the washer 50 of FIGS. 2B and 4B was pressed inward by tightening of the cap 58 to prevent the sheath from sliding), the stabilizer device 20 would thus be restrained against lateral (side-to-side) movement as well as longitudinal (distal/proximal) movement. If the sheath 128 or other instrument were relatively unrestrained longitudinally with the stabilizer device 20 (e.g., where the washer 50 of FIGS. 2B and 4B was not compressed against the sheath), the stabilizer device 20 would only be restrained against lateral (side-to-side) movement, thus permitting the sheath 128 to be held stable while allowing the stabilizer device 20 to move longitudinally responsive to similar longitudinal movement of the heart apex resulting from the beating of the heart.

Figure 9B:
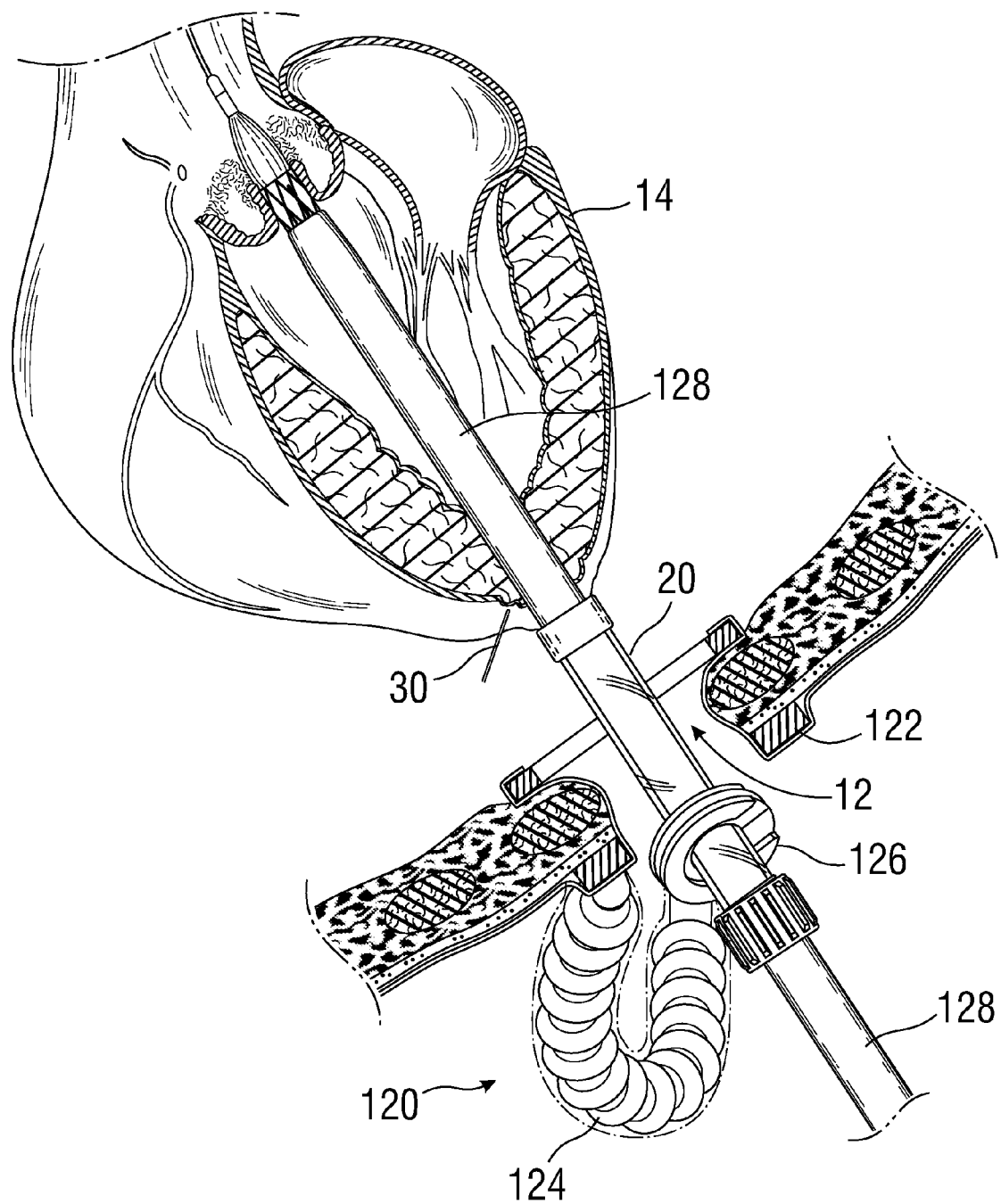

In another example depicted in FIG. 9B, the stabilizer arm 124 and cuff 126 is secured to the stabilizer device 20 of the invention in order to hold the stabilizer device 20 itself securely in a desired portion. If the sheath 128 or other instrument were relatively restrained longitudinally with respect to the stabilizer device 20 (e.g., where the washer 50 of FIGS. 2B and 4B were pressed inward by tightening of the cap 58 to prevent the sheath from sliding), the sheath 128 would thus be restrained against lateral (side-to-side) movement as well as longitudinal (distal/proximal) movement. If the sheath 128 or other instrument were relatively unrestrained longitudinally with the stabilizer device 20 (e.g., where the washer 50 of FIGS. 2B and 4B were not compressed against the sheath), the stabilizer device 20 would only be restrained against lateral (side-to-side) movement, thus permitting the stabilizer device 20 to be held stable while the sheath 128 could move longitudinally responsive to similar longitudinal movement of the target area of treatment within the heart.

In a further embodiment of the invention, a multiple-arm outside stabilizer could be used, such as the type depicted in FIGS. 14-18 of U.S. patent application Ser. No. 12/845,584. One stabilizer arm could be used to hold the stabilizer device 20, while another stabilizer arm could be used to hold the sheath 128 or other medical device. Accordingly, both the stabilizer device 20 and any medical device advanced therethrough would be firmly held in a desired position.

Figure 10A:
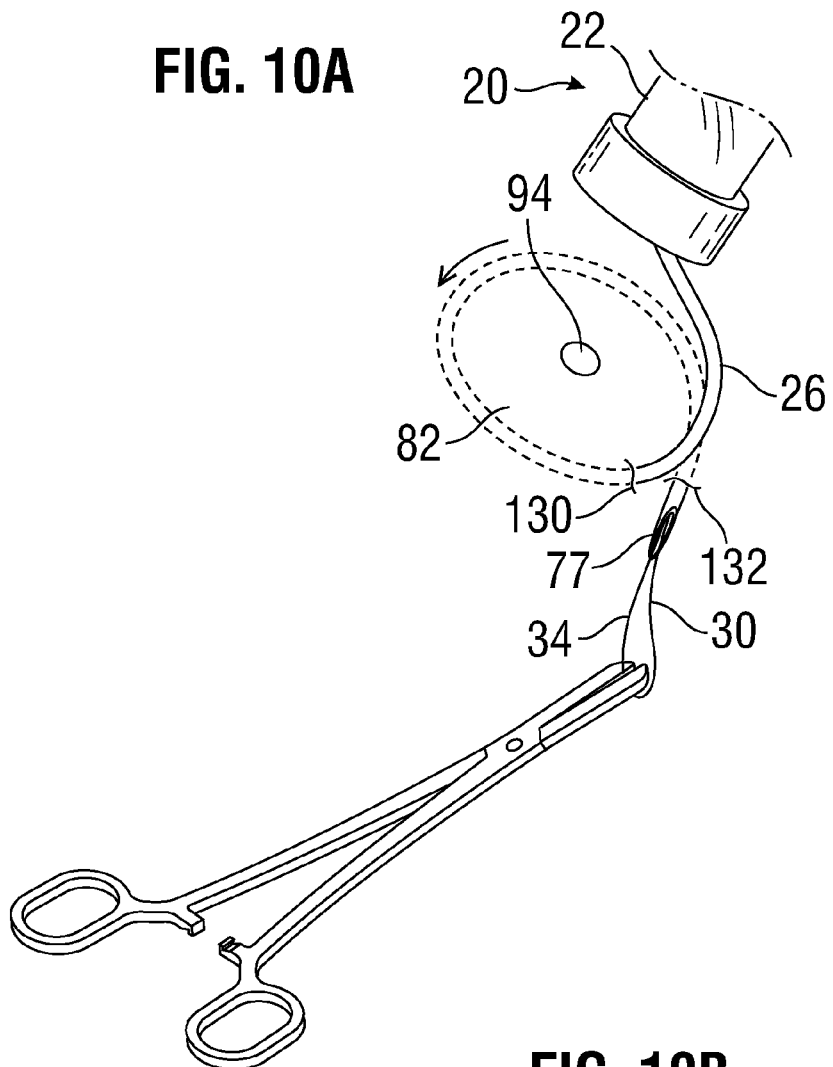
FIG. 10A depicts a perspective view of a stabilizer device being withdrawn from the heart wall according to an embodiment of the invention.
Figure 10B:
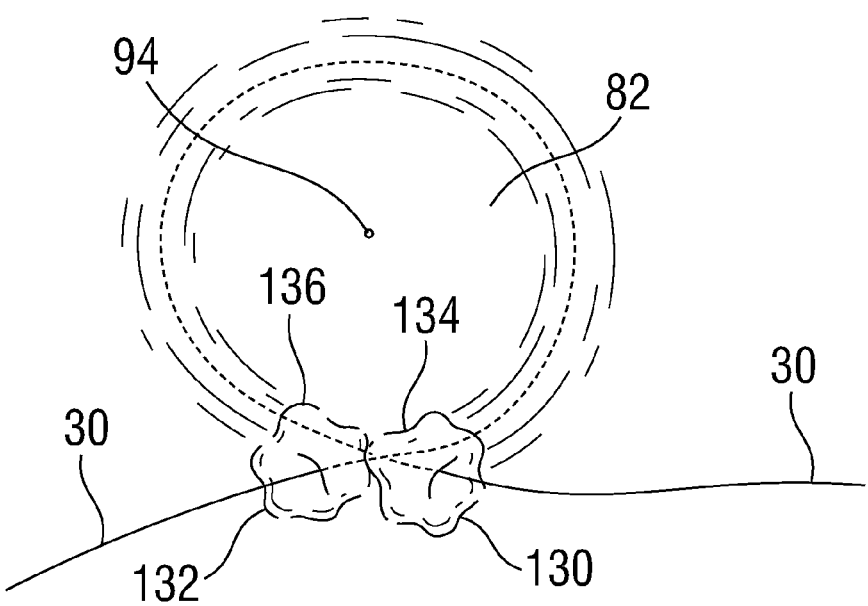
FIG. 10B is a front view of an apical puncture closed using suture according to an embodiment of the invention.

Once the desired procedure has been performed on the interior of the heart (such as the prosthetic heart valve deployment depicted in FIGS. 8A-8D), the device 20 is removed from the heart wall 82, as depicted in FIGS. 10A and 10B. To remove the helical needle 26 from the heart wall 82, the surgeon or other use rotates the device main body 22 to "unscrew" the device from the heart wall 82 about the apical puncture 94. For example, if the helical needle of the device was advanced into the heart wall by rotating the device in a clockwise direction, the user will now rotate the device in a counter-clockwise direction to remove the helical needle from the heart wall.

While holding the suture distal portion 34 (or with the suture distal portion otherwise secured, e.g., as by being sutured to the patient at a position outside the intercostal incision), the suture needle 26 is rotated in the opposite direction to reverse its path through the tissue. The length of suture 30 pays out from the stabilizer device 20. Once the helical needle 26 is completely out of the heart wall 82, the stabilizer device 20 is removed from the patient. Two free ends of the suture 30 (which could be single- or multi-stranded suture) extend from the entry point 130 and the exit point 132. As depicted in FIG. 10B, tensioning the suture 30 closes the apical puncture 94. The tensioned suture 30 can be secured with a knot or other securing technique/device. For example, pledgets 134, 136 may be added to the suture 30, which is then pulled tight and knotted adjacent the pledgets to close the puncture 94.

While the invention has been described in various embodiments, it is to be understood that the words which have been used are words of description and not of limitation. Therefore, changes may be made within the appended claims without departing from the true scope of the invention.

What is claimed is:

1. A method of accessing the interior of a heart using a device comprising an access port with at least one generally helical needle at a distal end thereof, the method comprising:
   positioning a distal end of the generally helical needle against an apex of the heart;
   advancing the generally helical needle into the heart wall at the apex of the heart without penetrating the interior of the heart, comprising rotating the helical needle in a first rotational direction with the distal end of the generally helical needle held against the apex of the heart;
   stabilizing the heart by securing the access port and generally helical needle in a generally fixed position;
   creating a puncture through the heart wall and into the interior of the heart at the apex of the heart using a puncture needle;
   advancing a treatment instrument into the interior of the heart via the access port and the puncture;
   performing a procedure on the heart using the treatment instrument;
   removing the treatment instrument from the interior of the heart;
   removing the generally helical needle from the heart wall at the apex of the heart, comprising rotating the generally helical needle in a second rotational direction, wherein the second rotational direction is opposite to the first rotational direction, wherein removing the generally helical needle from the heart wall occurs after performing the procedure on the heart using the treatment instrument.

2. The method of claim 1, wherein creating the puncture through the heart wall occurs after advancing the generally helical needle into the heart wall at the apex of the heart, and wherein the puncture is located in an area of the heart wall at least partially circumscribed by the generally helical needle.

3. The method of claim 1, wherein creating the puncture through the heart wall occurs before advancing the generally helical needle into the heart wall at the apex of the heart, and wherein the generally helical needle, as it advances into the heart wall, at least partially circumscribes the puncture through the heart wall.

4. The method of claim 1, wherein the device comprises a length of suture carried along the length of a distal portion of the generally helical needle, with a free end of the length of suture positioned at or adjacent a distal tip of the helical needle.

5. The method of claim 4, wherein the helical needle includes a deflection segment adjacent the distal tip that is more flexible than the rest of the distal portion of the helical needle, wherein the free end of the length of suture is at or adjacent the deflection segment, the method including deflecting the deflection segment in a proximal direction to direct the free end of the length of suture out of the heart wall tissue.

6. The method of claim 4, wherein the device further includes an inner needle arranged to translate through the helical needle and extend from the distal tip thereof, a portion of the length of suture positioned at the distal end portion of the inner needle, the inner needle having a relaxed shape at the distal end portion thereof that has a proximal bend so that it deflects in a proximal direction with respect to the helical needle when extended from the distal tip of the helical needle, the method including translating the inner needle along the helical needle so that the distal end portion of the inner needle extends from the distal tip of the helical needle and deflects in a proximal direction to direct the portion of the length of suture out of the heart wall tissue.

7. The method of claim 6, wherein the inner needle is hollow and the length of suture extends therethrough, the method including deflecting the distal end portion out of the tissue and grasping the portion of the length of suture.

8. The method of claim 4, further comprising:
   securing the free end of the length of suture at a position outside of the heart wall, wherein securing the free end of the length of suture occurs prior to removing the generally helical needle from the heart wall at the apex of the heart;
   after removing the generally helical needle from the heart wall, leaving a proximal portion of the length of suture extending from the point of entry of the helical needle;
   applying tension to the free end and proximal portion of the length of suture to cinch the heart wall tissue and close the puncture.

9. The method of claim 8, wherein the treatment instrument includes an introducer sheath carrying a heart valve, and performing a procedure on the heart comprises performing a heart valve replacement using the introducer sheath extending through the puncture.

10. The method of claim 1, wherein the site of puncture is the apex of a ventricle, and wherein the puncture needle includes an inner lumen and distal opening, and the method further comprises:
   installing a guidewire through the puncture needle inner lumen and into the ventricle;

wherein advancing the treatment instrument into the interior of the heart via the access port and the puncture comprises advancing the treatment instrument over the guidewire.

* * * * *